United States Patent [19]
DeCastro

[11] Patent Number: 5,830,127
[45] Date of Patent: Nov. 3, 1998

[54] METHOD AND APPARATUS FOR CLEANING ENDOSCOPES AND THE LIKE

[75] Inventor: Eugene A. DeCastro, Jamestown, N.Y.

[73] Assignee: Cybersonics, Inc., Jamestown, N.Y.

[21] Appl. No.: 689,014

[22] Filed: Aug. 5, 1996

[51] Int. Cl.[6] ........................................... A61B 1/12
[52] U.S. Cl. ..................... 600/157; 600/153; 604/267
[58] Field of Search ........................ 600/133, 153, 600/155, 156, 157, 158, 159; 604/267; 128/660.01, 662.03, 662.06; 433/86

[56] References Cited

U.S. PATENT DOCUMENTS

| | | | |
|---|---|---|---|
| 3,830,240 | 8/1974 | Antonevich et al. | 128/328 |
| 3,957,252 | 5/1976 | Storz | 259/1 R |
| 3,985,344 | 10/1976 | McCord | 259/1 R |
| 4,064,886 | 12/1977 | Heckele | 134/95 |
| 4,589,403 | 5/1986 | Ouchi et al. | 600/155 X |
| 4,870,953 | 10/1989 | DonMicheal et al. | 128/24 |
| 4,920,954 | 5/1990 | Alliger et al. | 128/24 |
| 5,240,675 | 8/1993 | Wilk et al. | 422/22 |
| 5,304,115 | 4/1994 | Pflueger et al. | 604/22 |
| 5,337,730 | 8/1994 | Maguire | 600/157 |
| 5,375,589 | 12/1994 | Bhatta | 128/4 |
| 5,462,604 | 10/1995 | Shibano et al. | 134/1 |
| 5,630,795 | 5/1997 | Kuramoto et al. | 600/157 X |

FOREIGN PATENT DOCUMENTS 4-312437  11/1992  Japan ..................................... 600/155

*Primary Examiner*—Beverly M. Flanagan
*Attorney, Agent, or Firm*—Bilicki & Simpson, P.C.

[57] ABSTRACT

A method and apparatus for ultrasonically cleaning the interior of a flexible, elongate, tubular medical instrument, such as an endoscope, laparoscope, or the like involves the generation of both longitudinal and transverse ultrasonic waves in a fluid medium within the interior channel or lumen of the instrument. The ultrasonic waves are generated within the instrument by a flexible wire resonator coupled to and responsive to an ultrasonic transducer and generator.

16 Claims, 3 Drawing Sheets

METHOD AND APPARATUS FOR CLEANING ENDOSCOPES AND THE LIKE

BACKGROUND OF THE INVENTION

1. Field of the invention

This invention relates to an improved method and apparatus for cleaning medical instruments. More particularly, the invention relates to a method and apparatus for ultrasonic cleaning of the interior channels of endoscopes and other medical instruments and devices.

2. Prior art

Medical procedures for the visualization of and surgery on internal body tissues and organs are commonly carried out with the aid of an elongate, flexible, tubular instrument which may be introduced into the body through an incision or natural opening. Such instruments include, for example, the endoscope, bronchoscope, cystoscope, gastroscope, laparoscope, and vaginoscope, as well as narrower bore instruments used for urethra catheterization, or cardiac catheterization.

The thorough cleaning of the lumen or working channel(s) of such instruments is difficult and traditional methods of cleaning are often inadequate and/or very time consuming. Among the traditional methods used for cleaning the internal channels of endoscopes and other such elongate tubular instruments, are the application of water jets and/or long brushes to loosen and remove contaminants such as dirt particles and the like prior to sterilization.

Often particulate contaminants are lodged in crevasses and corners within the instrument and are difficult or impossible to remove by such traditional physical methods of cleaning. Various studies have shown that traditional techniques for cleaning do not adequately remove pathogens and other contaminants prior to sterilization.

It is known that ultrasonic cleaning techniques can be used to supplement or replace traditional methods for cleaning medical instruments and the like. The application of ultrasonic energy to the cleansing of medical instruments such as endoscopes and the like is typically carried out by immersing the instruments in a cleansing tank filled with a cleaning fluid while generating ultrasonic vibrations in the cleaning fluid. The ultrasonic vibrations are created within the fluid by an ultrasonic resonator coupled to, and responsive to an ultrasonic generator or transducer. Typically, frequencies of about 18,000 to about 24,000 Hz are employed.

In the latter method, wherein the instrument to be cleaned is immersed in a cleaning fluid in an ultrasonic cleaning tank, the ultrasonic energy is applied in the fluid outside of the instrument. This approach may be adequate for instruments that have thin metal walls, but is generally less than adequate for cleaning the interior of large diameter nonmetallic instruments, especially those constructed of plastic materials. Many, or most, endoscopes and similar instruments are made of plastic. Plastic or polymeric materials attenuate the ultrasonic energy and prevent sufficient cavitational energy from reaching the lumen of the instrument and from dislodging contaminants in tight corners and crevasses in the interior channel(s) of elongated tubular instruments, such as endoscopes. Higher ultrasonic energy, sufficient to penetrate the wall of a plastic endoscope, may cause damage to the optical system enclosed in the wall. A more preferred method of ultrasonically cleaning the interior channel of an endoscope would be to direct ultrasonic energy directly into the channel by placing the open end near a source of focused ultrasonic energy. However, with such a method, most of the usable energy will be attenuated beyond a few centimeters into the working channel.

U.S. Pat. No. 3,957,252 discloses apparatus for cleaning medical instruments in a conventional sink. The apparatus comprises a an ultrasonic oscillator mounted on a support means to permit engagement of the oscillator with the washing water in the sink.

U.S. Pat. No. 5,380,369 to Steinhauser et al. discloses a process for cleaning and/or disinfecting medical instruments wherein an instrument to be cleaned is first washed internally and externally with a suitable cleansing liquid and the liquid then drained and the instrument dried with application of compressed air. Then—in the absence of a liquid medium—ultrasonic cleaning is applied.

U.S. Pat. No. 5,425,815 to Parker et al discloses a method of cleaning medical instruments comprising placing the instrument in an enclosure and applying a cleansing solution, and a disinfecting solution, then rinsing, purging and drying. The instrument may be pre-cleaned with the aid of a catheter delivering jets of water. Optionally, the catheter may be provided with an ultrasonic transducer.

U.S. Pat. No. 5,462,604 discloses a method for cleaning of workpieces immersed in a container of cleaning solution by a particular application of ultrasonic energy to produce cavitation in the cleaning solution, external to the workpieces being processed.

U.S. Pat. No. 4,016,436 to Shoh describes an ultrasonic processing apparatus wherein ultrasonic energy is applied to a tubular flexible resonator which, in turn, subjects a liquid within the resonator to intense vibratory energy from the wall of the resonator.

U.S. Pat. No. 4,537,511 to Frei discloses a hollow tubular resonator which may be employed in combination with a second resonator for producing ultrasonic energy in cleaning baths.

U.S. Pat. No. 5,200,666 to Walter at all discloses a rod-like resonator having ultrasonic generators coupled to each end. Both generators operate at the same frequency to transmit ultrasonic vibration to the resonator to be emitted radially therefrom.

U.S. Pat. No. 5,240,675 (Wilk et al) teaches a method for cleaning endoscopes with the aid of an elongate cleaning member containing an optical fiber for the transmission of sterilizing radiation; an electrical conductor for the transfer of heat energy into the channel; and a brush element to scrub the channel of the endoscope while a sterilizing fluid is passed through. The patentees additionally suggest vibrating the elongate cleaning member by the transmission of ultrasonic energy.

In addition to the prior art showing or suggesting various methods and apparatus for the application of ultrasonic energy in the cleaning of medical instruments and other devices or objects, the prior art discloses the use of ultrasonic "probes" and the like, such as, wires coupled to and extending from an ultrasonic transducer for various purposes, such as the for application of ultrasonic energy within narrow channels such as human blood vessels, urinary tracts and the like for the removal of blockages.

U.S. Pat. No. 4,572,184 to Stohl et al discloses an ultrasonic wire wave guide attachment device, for attaching a wave guide or wire to a power source such as an ultrasonic transducer. The attachment device comprises a screw having an axial passage therethrough providing a slip fit with the wire. The wire is passed into the axial passage and fastened by means of a metallurgical bonding material such as braze alloy or solder. The transducer is provided with a threaded opening to receive the attachment screw. The wave guide is preferably a cobalt base alloy.

U.S. Pat. No. 4,474,180 to Angulo discloses apparatus for disintegrating kidney stones be application of ultrasonic energy. The patentee teaches various means for attaching an ultrasonic wave guide, in the form of a wire probe, to an ultrasonic transducer, using set screws and the like.

U.S. Pat. No. 3,830,240 and 3,861,391, both to Antonevich et al, disclose ultrasonic method and apparatus for disintegration of urinary calculi. The patents teach the use of a wave guide, in the form of a wire, adapted to be inserted through a catheter. The patents further teach various methods of attachment of the wave guide to an ultrasonic transducer.

U.S. Pat. No. 4,870,953 to DonMichael et al discloses an apparatus and method for treating atherosclerotic plaque and intravascular blood clots by the application of ultrasonic energy. The ultrasonic apparatus employed includes a solid wire probe having a bulbous tip at one end and coupled to an ultrasonic energy source at the other end. The probe is carried within a hollow catheter to a site of stenosis. At this point, the probe is extended from the catheter and caused to vibrate ultrasonically, resulting in the destruction of the plaque or blood clot.

U.S. Pat. No. 4,920,954 to Alliger et al discloses an ultrasonic device for generating and applying cavitational force. The device comprises a solid wire wave guide, a transducer, a generator, and a handpiece enclosing the transducer. The solid wire wave guide is titanium. The device is employed in conjunction with a catheter assembly to introduce the titanium wire wave guide into a human artery where the longitudinal vibration of the wire causes an axial movement of the tip portion of the wire to produce a cavitational force for the removal of plaque. The wire material (titanium) and the design of the device are selected to minimize transverse ultrasonic vibration waves.

It is disclosed that the device may be used for other purposes, such as, for the removal of unwanted contaminants from inaccessible areas.

U.S. Pat. No. 5,304,115 to Russell et al discloses an ultrasonic angioplasty device comprising an elongate ultrasound wire transmission member having a bulbous head which may be inserted in and advanced through a catheter to a point slightly beyond the distal end of the catheter. The wire serves to transmit longitudinal ultrasonic energy to the bulbous head where the energy effects an ablative treatment of an occluding arterial deposit such as plaque.

It will be apparent to those skilled in the art that although the prior art teaches a variety of useful methods and apparatus, including various ultrasonic methods and apparatus, for cleaning objects such as medical instruments, more efficient methods for cleaning the interior channels of elongated tubular instruments, such as endoscopes, is desirable.

It is an object of the present invention to provide an improved method and apparatus for cleaning the interior channels of elongated tubular medical instruments, such as endoscopes.

It is a further object to provide a method and apparatus for the generation of both transverse and longitudinal ultrasonic wave energy within the interior channel(s) of an endoscope or the like.

It is a still further object to provide a method and apparatus for the cleaning of the interior channel or lumen of an endoscope or other elongate tubular instrument wherein cavitational cleaning action is generated at a multiplicity of sites along the length of the interior channel of the endoscope simultaneously.

SUMMARY OF THE INVENTION

The present invention provides a process and apparatus for the ultrasonic cleaning of the interior channel of a flexible, tubular instrument, such as an endoscope.

The process of the invention comprises filling the interior channel or lumen of the instrument with a cleaning fluid and producing transverse and longitudinal ultrasonic waves within the fluid-filled lumen. Ultrasonic waves and cavitation are produced in response to the vibratory motion of a flexible, wire resonator positioned within the fluid-filled lumen of the instrument to be cleaned.

The apparatus of the present invention comprises a flexible, wire ultrasonic resonator having a distal end and a proximal end, adapted to be inserted at its distal end into the interior channel of an endoscope or other elongate tubular instrument. The flexibility of the wire resonator of the present invention provides an advantage in allowing the resonator to be inserted into an elongate tubular instrument that may be in a curved, or even coiled, configuration and to adapt or conform to such shape without damage to the instrument.

An important characteristic of the apparatus of the present invention is the ability of the wire resonator to generate both transverse and longitudinal ultrasonic vibrations simultaneously. At its proximal end the resonator is coupled to an ultrasonic transducer, which in turn is powered by an ultrasonic power generator. The flexible resonator, in response to the transducer, produces substantial transverse vibrations at positions along its entire length, as well as longitudinal vibrations at its distal end. Within the liquid-filled lumen of the instrument to be cleaned, the combination of ultrasonic transverse and longitudinal wave motion causes a turbulence that results in cavitational cleaning action in the liquid.

The transverse vibrations, which occur at antinode positions along the length of the wire resonator, generate cavitational cleaning action in the liquid at each position. As a result, cavitational cleaning action occurs simultaneously at a multiplicity of sites within the interior channel or lumen of the instrument. The cavitational action within the liquid in the channel of the instrument facilitates and accelerates the detachment of contaminants such as particles embedded or trapped in crevasses and corners.

During the ultrasonic cleaning process, liquid is passed through the lumen or channel being cleaned. In a typical cleaning procedure, transverse and longitudinal ultrasonic vibrations are produced by the resonator within the lumen or channel to be cleaned, while a liquid, for example, an aqueous solution of a suitable sterilant, disinfectant, and/or cleaning agent is passed through an irrigation port into the proximal end of the lumen and allowed to pass out through the distal end.

In the operation of the transducer, a pulsed mode is preferred to continuous wave mode. In the pulsed mode (e.g. 50% on; 50% off) the cleaning fluid is degassed very quickly and increases the effects of ultrasonic cavitation.

The flexible resonator is a solid rod-like or wire member composed of a metallic material capable of producing both transverse and longitudinal ultrasonic waves in response to the action of an ultrasonic transducer. Preferred materials for this purpose include metals or alloys such as nickel or nickel cobalt alloys characterized by a high modulus of elasticity or materials that can be treated, such as by coldworking and/or heat treatment to achieve a high modulus of elasticity, preferably greater than 18 million psi. Such materials are more readily excited into transverse ultrasonic motion at lower stress levels, thus reducing the energy necessary to produce high levels of transverse motion. Higher stresses and power levels would be required to produce transverse motion in titanium alloys. At lower power levels, less heat is generated, thus reducing heating of the ultrasonic resonator and increasing the resonator life. Especially useful for this purpose are alloys of nickel/cobalt/chrome/molybdenum such as MP-35N alloy or Elgiloy. A most preferred material is Elgiloy (a cobalt alloy containing about 0.15% C, 20% Cr, 15% Ni, 15% Fe, 7.0% Mo and 0.04% Be) wire that has been 48% cold reduced and heat treated at 980° F. for about five hours. The advantages of the resonator material employed in the apparatus of the present invention over the materials employed in prior art devices is further illustrated by reference to the following table:

TABLE 1

| Alloy | Modulus of Elasticity (EOü × $10^6$ PSI) | Endurance Limit × $10^3$ PSI | Tensile Strength × $10^3$ PSI |
|---|---|---|---|
| Ti (6 L-4 V) | 15–17 | 60–85 | 130 |
| Stainless Steel | 28 | 39 | 85–90 |
| Elgiloy | 29.5 | NA | 230–250 |

The diameter of the rod or wire that constitutes the flexible resonator of this invention is typically about 0.010–0.100 inches and preferably about 0.015–0.060 inches in diameter. To provide an even higher degree of flexibility, for situations where the resonator must be inserted in, and conform to the shape of, a tightly coiled endoscope, the wire diameter is preferably in the range of about 0.025–0.035 inches.

The length of the flexible wire resonator may vary but is preferably greater than the length of the endoscope channel to be cleaned and is advantageously a multiple of the wave length of the driving frequency and selected as necessary to terminate the end of the resonator at a longitudinal antinode position.

The operating frequency may vary considerably and will typically be in the range of about 15,000 to 100,000 Hz. in general, the lower the frequency, the stronger the cavitation action and the more thorough the cleaning action. The higher the frequency, the weaker the cavitation action and the less potential for cavitation damage to the instrument being cleaned. At lower frequencies, the space between transverse antinodes is greater while at higher frequencies the space between transverse antinodes is less. A typical operating frequency is about 20,000 Hz for a solid flexible resonator made of Elgiloy, 15 inches long and 0.035 inches diameter. Other operating frequencies can be used. The lengths are proportioned as necessary to terminate the end of the resonator at a longitudinal motion antinode position. At 20,000 Hz a solid 0.035 inch diameter wire produces concentric transverse motion at intervals of about every 0.5 inches along the length of the resonator. For a 15 inch long resonator, 25 transverse antinode positions are produced. Using the same wire length and driving frequency, but with a wire diameter of 0.020 inches, concentric transverse wave motion is produced at intervals of about 0.325 inches along the entire length of the resonator. About 46 transverse antinode positions are produced.

The transverse half wave lengths of a fixed free bar, such as a wire resonator attached at one end to a transducer, can be determined theoretically by the following equation:

$$\tfrac{1}{2}\lambda = [(C_n C_c d/2)/2F]^{\tfrac{1}{2}}[1/(n-1)]$$

where $C_n$ (boundary condition) $= [(2n-1)/8]\pi$; $n = \tfrac{1}{2}\lambda$; where $\lambda = C_c/F$; n=bar length; $C_c$=bar velocity; d=diameter; F=driving frequency.

The wire resonator is attached at its proximal end to a transducer. The attachment may be made by various techniques known in the prior art, such as, by brazing, soldering, cementing, as with epoxy cement, or with set screw or clamping means or the like. Among the various means of attachments that may be employed are those set forth in U.S. Pat. No. 4,572,184; 4,474,180; 3,380,240; and 3,861,391; all referred to hereinabove. In a preferred embodiment of the apparatus of the present invention the attachment is made by means of a crimp screw that is threaded on one end (to be screwed into a threaded hole in the transducer) and provided with a hole in the other end into which the proximal end of the wire resonator may be inserted. The end of the crimp screw into which the wire is inserted is then crimped around the wire to provide a tight pressure attachment. The attachment device produces a mismatch boundary condition which reduces the longitudinal motion and promotes transverse wave generation.

In an alternate embodiment, the apparatus may comprise a multiplicity of wire resonators attached to the transducer.

The wire, preferably Elgiloy, may advantageously be provided with a protective coating which may be a hard coating, such as titanium nitride, or a soft coating such as polytetrafluoroethylene (Teflon; fluon; etc.) or the like to protect it from damage due to the cavitational action of the liquid. Hard coatings such as titanium nitride have the advantage of minimizing attenuation of the ultrasonic energy and are preferred.

In a preferred embodiment a series of beads, preferably plastic beads, are disposed along the length of the resonator wire, as a protection means, to prevent the resonator wire from contacting the inner wall of the endoscope during the cleaning operation. The beads may be attached to the wire by various methods, for example, by means of an adhesive, or during fabrication by molding directly on to the wire. The beads are positioned at node points along the wire. The plastic beads, positioned in this manner will not interfere with the generation of transverse motion.

The apparatus of the present invention is further illustrated by the following detailed description and accompanying drawings.

DETAILED DESCRIPTION

Figure 1:
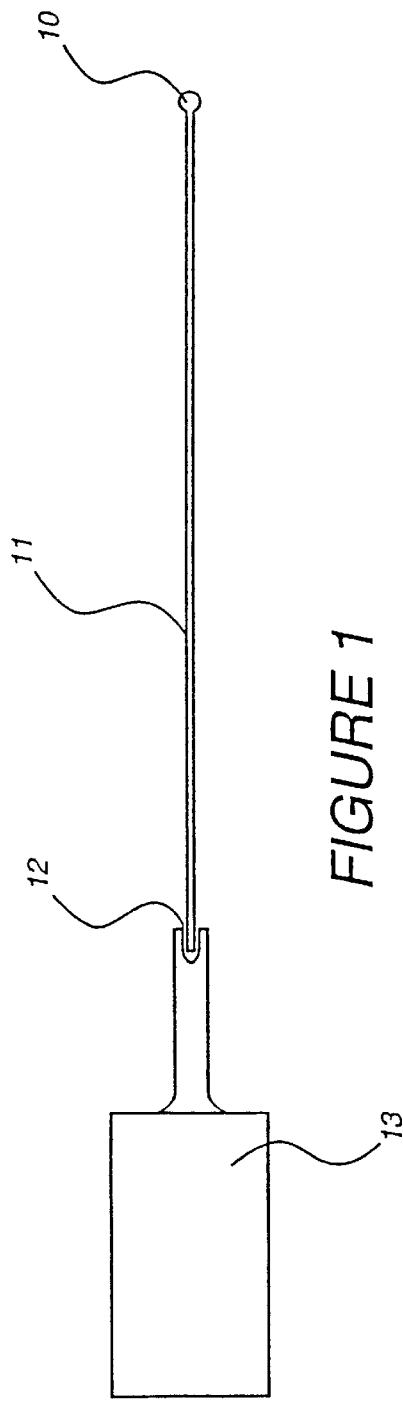
FIG. 1 is a longitudinal sectional view of an ultrasonic resonator of the present invention coupled at its proximal end to an ultrasonic generator.

Referring now to the drawings in detail: In FIG. 1 a wire resonator or wave guide (11) is shown attached at its proximal end (12) to an ultrasonic transducer (13). The ultrasonic transducer may be of the magnetorestrictive type or, preferably, of the piezoelectric type. The ultrasonic resonator (11) is a flexible wire of a material capable of producing both transverse and longitudinal vibrations in response to ultrasonic transducer (13). In a preferred embodiment, the wire resonator is terminated in a ball shape (10) at the distal end to provide a smooth surface and thus serve to protect the internal wall of the endoscope as the resonator is passed therethrough.

Figure 2:
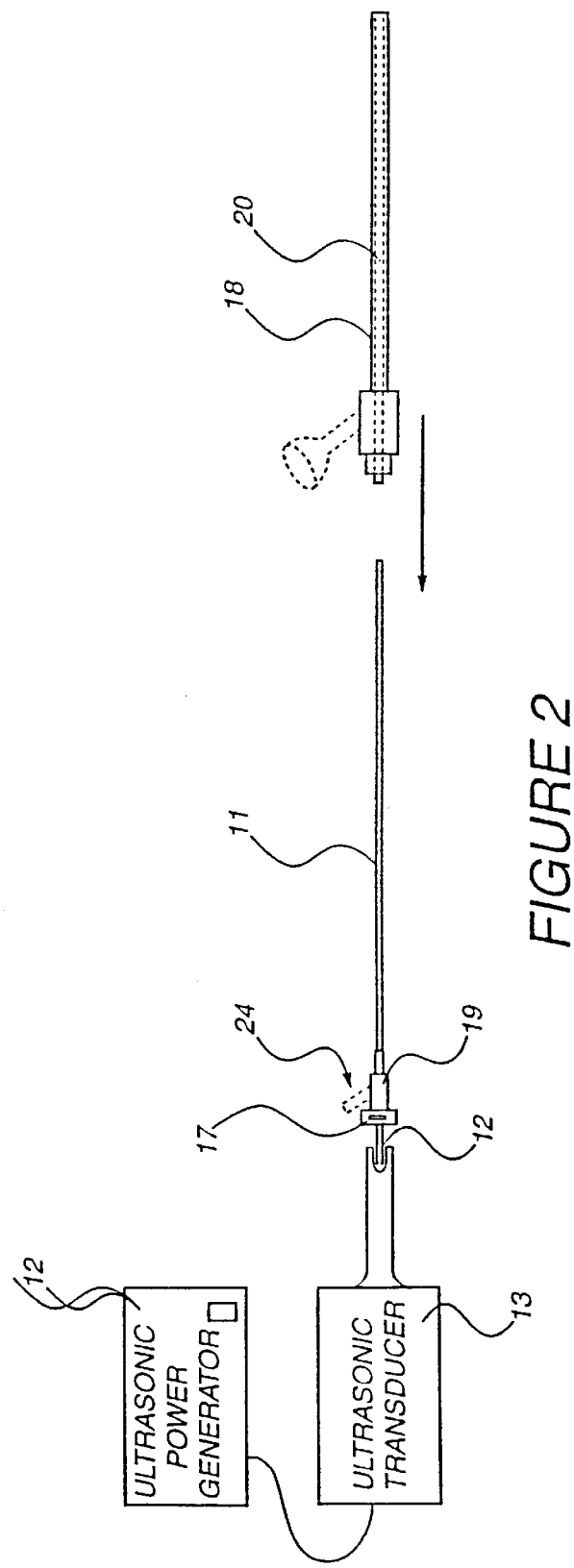
FIG. 2 is a longitudinal view of the ultrasonic resonator and generator of the present invention with the resonator positioned within the interior channel of a rigid or flexible endoscope to be cleaned and having a "Y" connector assembled over the proximal region of the resonator.

FIG. 2 is a longitudinal sectional view of the ultrasonic resonator (11) attached at its proximal end (12) to the ultrasonic transducer (13), which, in turn, is shown connected to an ultrasonic power generator (16). The resonator (11) is shown positioned in axial alignment with the endoscope (18) to be cleaned. A "Y" connector (19) is assembled over the resonator and may provide a fluid access means such as irrigation port (24) to permit irrigation of the endoscope channel (20) with cleaning solution during the cleaning operation. The "Y" connector through which the resonator (11) may be inserted contains a seal (17) to prevent leakage from the connector during use.

Figure 3:
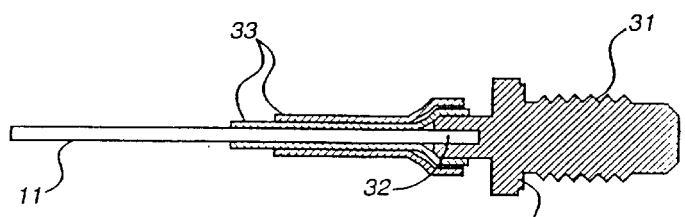
FIG. 3 is a sectional view of the proximal end of the ultrasonic resonator showing a preferred means of attachment to an ultrasonic transducer.

The solid flexible resonator (11) may be attached at the proximal end to the tip of the ultrasonic transducer (13) by various means. A preferred form of attachment, as depicted in FIG. 3, is a crimp screw (14) which is provided with threads (31) at one end and a hole (32) at the other end. The hole (32) is adapted to receive the proximal end of the wire resonator (11). When the end of resonator (11) is positioned in hole (32) the end of the crimp screw (14) is crimped to provide a pressure attachment. The other end of the crimp screw (14) is provided with threads (31) which may be conveniently screwed into a compatible threaded opening (not shown) in the end of the transducer (13). FIG. 3 further shows two layers of plastic tubing (33) which may, for example, be of Teflon to provide protection and to attenuate the ultrasonic energy at the attachment site, reducing the possibility of failure at the attachment site.

Figure 4:
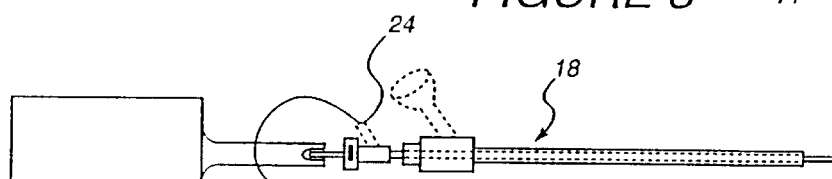
FIG. 4 is a sectional view of the ultrasonic resonator together with various cleaning, washing, and disinfecting means.

During the cleaning operation, the endoscope (18) being cleaned may be supplied with various liquid cleaning and rinsing agents, preferably aqueous, such as, disinfectants, detergents, rinse water and the like from a source such as pump (15) through irrigation port (24) as shown in FIG. 4.

Figure 5:
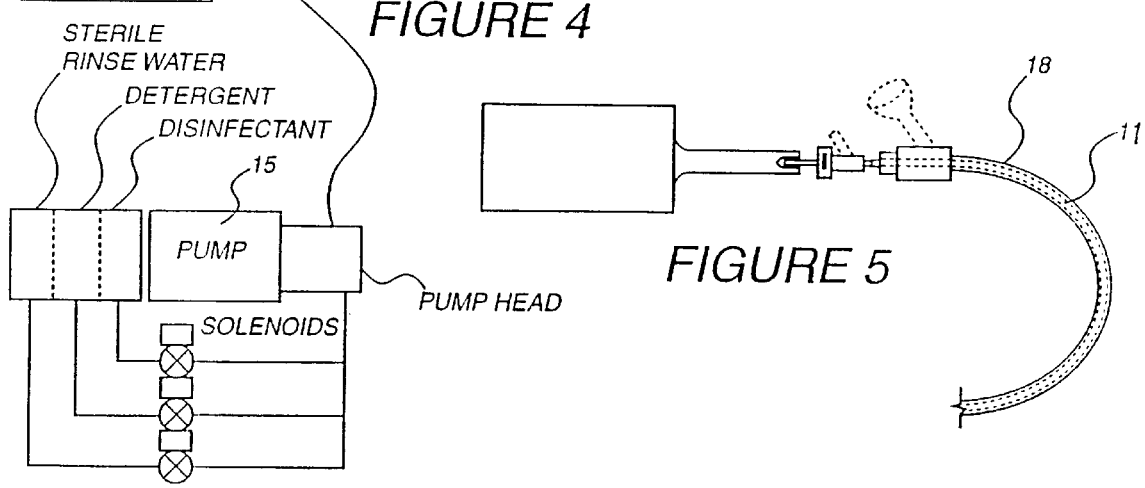
FIG. 5 is a longitudinal sectional view of the flexible resonator and generator with the flexible resonator positioned within the interior channel of a flexible endoscope in a curved configuration.
Figure 6:
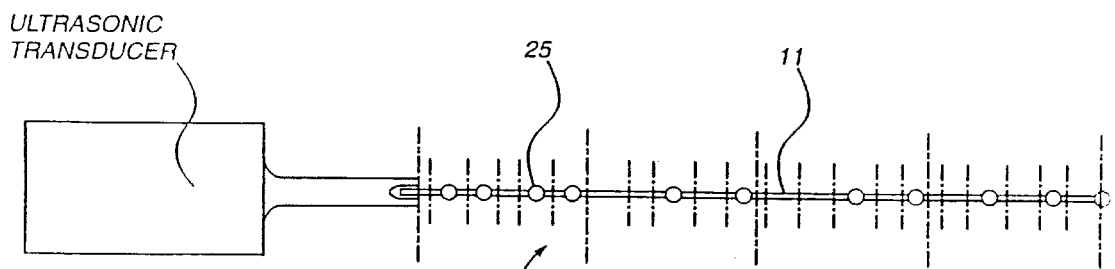
FIG. 6 is a longitudinal sectional view of the flexible resonator in a preferred embodiment wherein a series of beads are positioned at node points along the length of the resonator to prevent the resonator from contacting the inner wall of the endoscope.

The wire resonator (11) is flexible and able to conform to the changeable contours of a flexible endoscope (18) shown in a curved configuration in FIG. 5. The flexible wire resonator (11) as depicted in FIG. 6 represents a preferred embodiment wherein a series of beads (25) are positioned at node points along the length of the resonator to prevent the vibrating resonator from contacting and possibly damaging the inner wall of the endoscope during cleaning. The beads (25) are preferably of a plastic material. When the beads are positioned properly, that is, at node points, along the resonator, they will not interfere with the generation of transverse motion, but will serve to protect the inner surface of the endoscope being cleaned.

Figure 7:
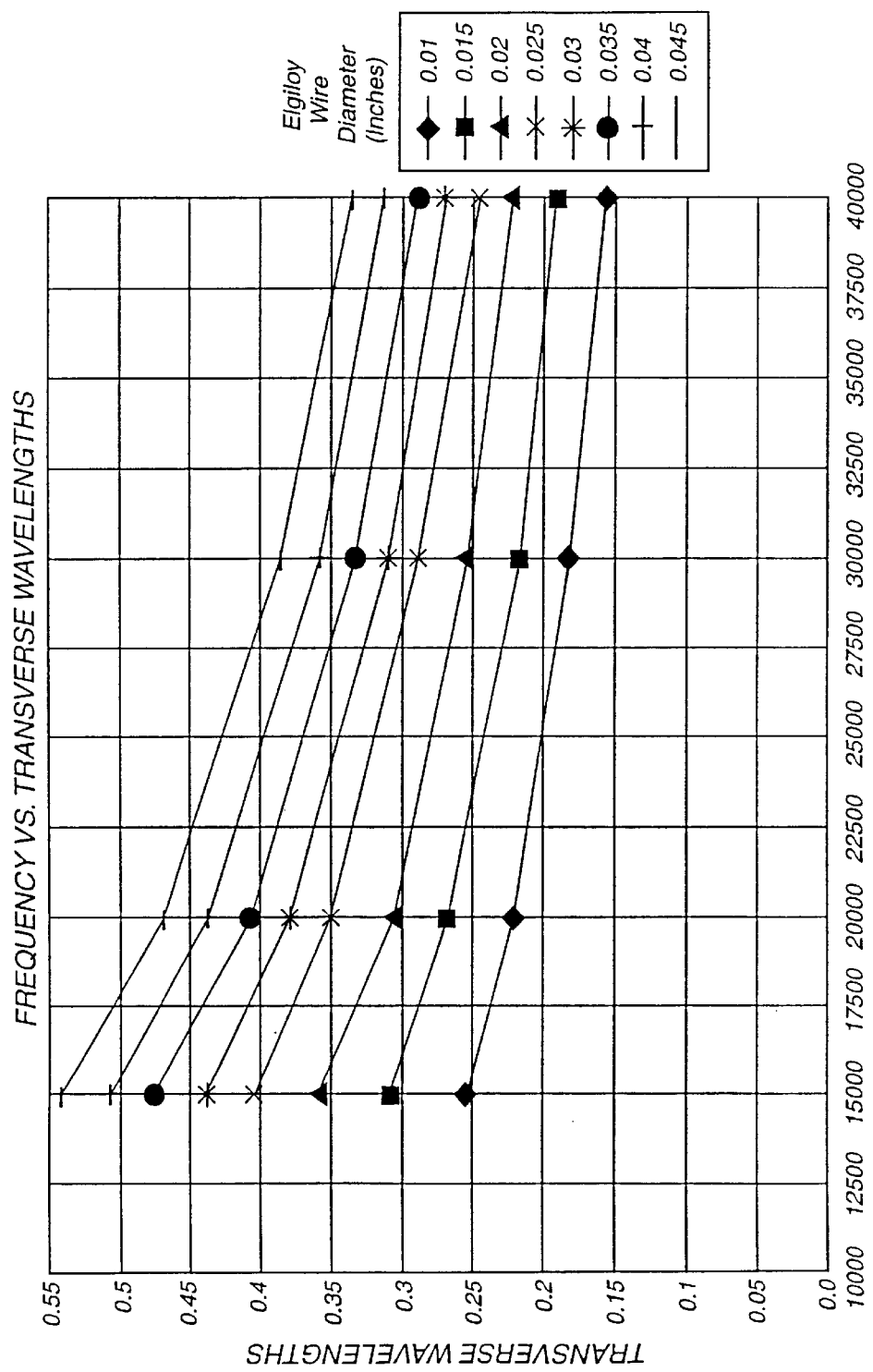
FIG. 7 is a plot of driving frequency and transverse wave lengths for various wire diameters of Elgiloy wire.

The relationship between the operating or driving frequency and the transverse wavelength for wires of a given material and various diameters is shown in FIG. 7. In the chart, transverse wavelength (inches) is plotted against driving frequency (Hz) for various diameters of Elgiloy wire. The Elgiloy wire employed was 48% cold reduced and heat treated at 980° F. for about five hours.

Although, for convenience, the method and apparatus of the present invention have been described hereinabove primarily with respect to the cleaning of endoscopes, it will be apparent to those skilled in the art that the invention applies also the many similar instruments characterized by an elongate tubular configuration as well as to other situations and devices wherein contaminants may be difficult to dislodge or remove by traditional cleaning methods.

We claim:

1. A process for the cleaning of the interior channel of an elongate tubular instrument comprising: generating both longitudinal and transverse ultrasonic waves in a liquid medium from within the interior channel, wherein the longitudinal and transverse ultrasonic waves are generated within the interior channel of the elongate tubular instrument by a flexible solid metal wire within the interior channel of the elongate tubular instrument by a flexible solid metal wire resonator positioned therein, the resonator being coupled to and responsive to an ultrasonic transducer, wherein cavitational cleaning action is generated in the liquid medium by ultrasonic energy produced simultaneously at a multiplicity of transverse antinode sites along the length of the flexible solid wire resonator.

2. A process according to claim 1 wherein the liquid medium is an aqueous liquid.

3. A process according to claim 1 wherein the elongate tubular instrument is an endoscope.

4. A process according to claim 2 wherein the ultrasonic transducer is operated in a pulsed mode.

5. A process according to claim 2 wherein the operating frequency of the flexible solid metal wire resonator and ultrasonic transducer is in the range of about 15,000 Hz to about 100,000 Hz.

6. A process according to claim 2 wherein an aqueous liquid cleaning agent is caused to flow through the interior channel of the elongate tubular instrument during the process.

7. An ultrasonic resonator adapted for positioning within a liquid-filled interior channel of an elongate tubular instrument, the resonator comprising: a flexible, elongate solid metal wire capable of generating both transverse and longitudinal ultrasonic vibrations to produce cavitational action in the liquid-filled interior channel at a multiplicity of transverse antinode sites along the length of the flexible, elongate solid wire resonator in response to an ultrasonic transducer.

8. An ultrasonic resonator according to claim 7 adapted for entry into the interior channel of an endoscope and provided with an irrigation port through which liquid may be caused to enter the interior channel.

9. An ultrasonic resonator according to claim 7 comprising a nickel/cobalt alloy wire characterized by a modulus of elasticity greater than about 18 million psi.

10. An ultrasonic resonator according to claim 9 comprising Elgiloy wire.

11. An ultrasonic resonator according to claim 9 having a diameter in the range of about 0.015 to about 0.060 inches.

12. An ultrasonic resonator according to claim 9 characterized by at least one protective coating on at least a portion of the surface thereof.

13. An ultrasonic resonator according to claim 12 wherein the protective coating is polytetrafluoroethylene.

14. An ultrasonic resonator according to claim 12 wherein the protective coating is titanium nitride.

15. A process for the cleaning of the interior channel of an elongate tubular instrument comprising: generating both longitudinal and transverse ultrasonic waves in a liquid medium from within the interior channel, wherein the longitudinal and transverse ultrasonic waves are generated within the interior channel of the elongate tubular instrument by a flexible solid metal wire resonator positioned therein, the resonator being coupled to and responsive to an ultrasonic transducer, and wherein a series of plastic beads are positioned at transverse node points along the length of the wire resonator.

16. An ultrasonic resonator adapted for positioning within a liquid-filled interior channel of an elongate tubular instrument, the resonator comprising: a flexible, elongate solid metal wire capable of generating both transverse and longitudinal ultrasonic vibrations to produce cavitational action in the liquid-filled interior channel at a multiplicity of transverse antinode sites along the length of the flexible, elongate solid wire resonator in response to an ultrasonic transducer, wherein a series of plastic beads are positioned at transverse node points along the length thereof.

* * * * *